(12) United States Patent
Wegerer et al.

(10) Patent No.: US 8,258,356 B2
(45) Date of Patent: Sep. 4, 2012

(54) SELECTIVE CO OXIDATION FOR ACETYLENE CONVERTER FEED CO CONTROL

(75) Inventors: David A. Wegerer, Lisle, IL (US); Kurt Vanden Bussche, Lake in the Hills, IL (US)

(73) Assignee: UOP LLC, Des Plaines, IL (US)

( * ) Notice: Subject to any disclaimer, the term of this patent is extended or adjusted under 35 U.S.C. 154(b) by 176 days.

(21) Appl. No.: 12/857,709

(22) Filed: Aug. 17, 2010

(65) Prior Publication Data

US 2012/0046507 A1 Feb. 23, 2012

(51) Int. Cl.
C07C 5/08 (2006.01)
(52) U.S. Cl. .................... 585/254; 585/250; 585/259
(58) Field of Classification Search .............. None
See application file for complete search history.

(56) References Cited

U.S. PATENT DOCUMENTS

| | | | |
|---|---|---|---|
| 6,673,742 B2 | 1/2004 | Abdo et al. | |
| 6,692,713 B2 | 2/2004 | Grunwaldt et al. | |
| 7,009,085 B2 | 3/2006 | Cheung | |
| 7,189,373 B2 | 3/2007 | Taniguchi et al. | |
| 7,453,017 B2 | 11/2008 | Moon et al. | |
| 7,541,311 B2 | 6/2009 | Chen et al. | |
| 7,572,304 B2 | 8/2009 | Wheat et al. | |
| 7,915,461 B2 * | 3/2011 | Gattis et al. | 585/324 |
| 2005/0096217 A1 | 5/2005 | Rokicki et al. | |
| 2008/0078692 A1 | 4/2008 | Wegerer et al. | |
| 2009/0194459 A1 * | 8/2009 | Vincitore et al. | 208/97 |

OTHER PUBLICATIONS

Park, Y.H. et al., A Deuterium Tracer Study on the Effect of CO on the Selective Hydrogenation of Acetylene over Pd/Al2O3, Industrial & Engineering Chemistry Research, vol. 30, No. 8, pp. 1693-1699, dated Aug. 1991, American Chemical Society (ACS).
Park, Y.H., "A study on the effects of additives on slective hydrogenation of trace acetylene over palladium catalysts", Louisiana State University & Agricultural & Mechanical College, Dissertation (1991) 219P (Order from University Microfilms International as No. DA9200082) (Abstract) Dissertation Abstracts International: Section B Science & Engineering (ISSN 0419-4217), vol. 52, No. 7, pp. 3763-B, dated Jan. 1992.
Sasaki, K. et al., "Effects of Selectivity on Acetylene Removal Unit Plant Operations", AIChE 9th Ehtylene Producers Conference (1997) Proceedings vol. 6, pp. 271-290, dated 1977.
McGown et al., The Hydrogenation of Acetylene in Excess Ethylene on an Alumina-Supported Palladium Catalyst in a Static System, J. Chem. Soc. Faraday Trans, vol. 73, No. 4, pp. 632-647, dated 1977 Faraday Division of the Chemical Society.

* cited by examiner

*Primary Examiner* — Tam M Nguyen
(74) *Attorney, Agent, or Firm* — Arthur E Gooding

(57) ABSTRACT

A system and process for acetylene selective hydrogenation of an ethylene rich gas stream. An ethylene rich gas supply comprising at least $H_2S$, $CO_2$, CO, and acetylene is directed to a first treatment unit for removing $H_2S$ and optionally $CO_2$ from the gas stream. A CO oxidation reactor is used to convert CO to $CO_2$ and form a CO-depleted gas stream. A second treatment unit removes the $CO_2$ from the CO-depleted gas stream and an acetylene selective hydrogenation treats the CO-depleted gas stream.

10 Claims, 3 Drawing Sheets

SELECTIVE CO OXIDATION FOR ACETYLENE CONVERTER FEED CO CONTROL

FIELD OF THE INVENTION

The invention relates to a system for reducing CO concentration in an ethylene rich stream.

DESCRIPTION OF RELATED ART

Industrial processes for producing ethylene include catalytic and thermal cracking of hydrocarbon feedstocks. In at least some cases, the cracking process effluent contains carbon monoxide. For example, certain product separation and recovery systems produce a vapor stream rich in ethylene and containing hydrogen, methane, acetylene, ethane and other contaminants such as CO, $CO_2$, and $H_2S$ that must be removed in order to produce a high purity ethylene product. Acetylene in polymer grade ethylene is typically limited to a maximum of 5 vol ppm. A typical polymer grade ethylene specification is shown in Table 1.

TABLE 1

| Typical Polymer Grade Ethylene Specifications | |
|---|---|
| Ethylene | 99.90 vol % min |
| Methane plus ethane | 1000 vol ppm max |
| Ethane | 500 vol ppm max |
| Acetylene | 5 vol ppm max |
| C3 and heavier | 10 vol ppm max |
| CO | 2 vol ppm max |
| $CO_2$ | 5 vol ppm max |
| Sulfur | 2 wt ppm max |

Acetylene removal is typically effected by acetylene conversion to ethylene via selective hydrogenation. Carbon monoxide (CO) attenuates the activity of the commonly used acetylene selective hydrogenation catalysts and thus excessive CO concentration can be problematic.

Hence it would be beneficial to be able to control the amount of CO that enters the acetylene conversion unit.

SUMMARY OF THE INVENTION

The present invention relates to controlling CO concentration in a stream prior to subjecting the stream to an acetylene selective hydrogen catalyst.

One embodiment of the invention is directed to a system for acetylene selective hydrogenation of an ethylene rich gas stream comprising: (a) an ethylene rich gas supply comprising at least $H_2S$, $CO_2$, CO, and acetylene; (b) a first treatment unit for removing $H_2S$ and, optionally, $CO_2$ from the gas stream; (c) a CO oxidation reactor to convert CO to $CO_2$ and forming a CO-depleted gas stream; (d) a second treatment unit for removing the $CO_2$ from the CO-depleted gas stream; and (e) an acetylene selective hydrogenation downstream of the CO oxidation reactor.

Another embodiment of the invention is directed to a process for acetylene selective hydrogenation of an ethylene rich gas stream comprising: (a) supplying an ethylene rich gas comprising at least $H_2S$, $CO_2$, CO, and acetylene to a first treatment unit and removing $H_2S$ and, optionally, $CO_2$ from the gas stream; (b) supplying the $H_2S$ and $CO_2$ free gas stream to an CO oxidation reactor and converting CO to $CO_2$ to form a CO-depleted gas stream; (c) supplying the CO-depleted gas stream to a second treatment unit to remove the $CO_2$ from the CO-depleted gas stream; and (d) treating the CO-depleted or CO-depleted gas stream to an acetylene selective hydrogenation unit to convert the acetylene to ethylene.

These and other embodiments relating to the present invention are apparent from the following Detailed Description.

BRIEF DESCRIPTION OF THE DRAWINGS

The same reference numbers are used to illustrate the same or similar features throughout the drawings. The drawings are to be understood to present an illustration of the invention and/or principles involved.

DETAILED DESCRIPTION

Figure 1:
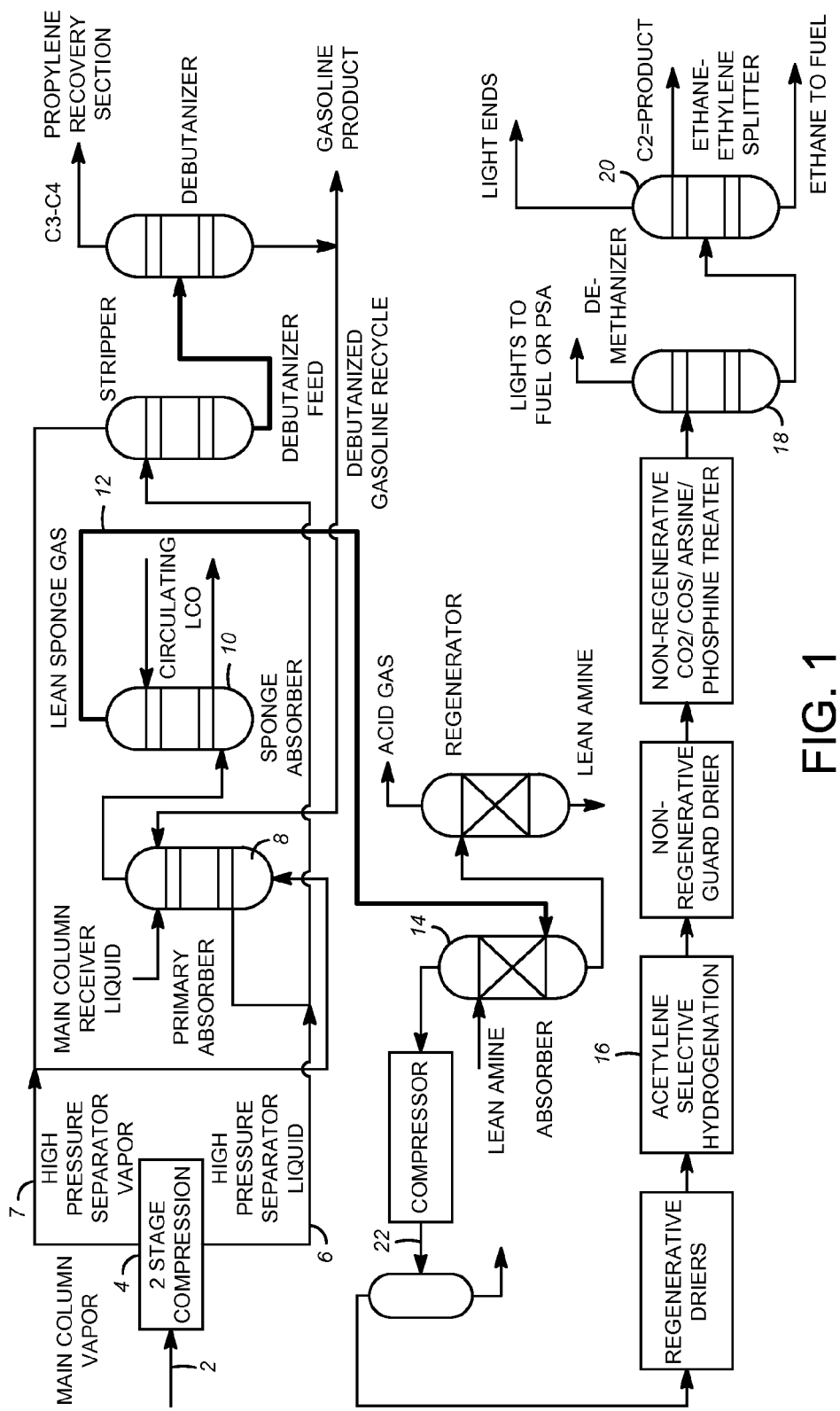
FIG. 1 is a schematic of part of a PetroFCC™ product treating and recovery system.

FIG. 1 is a schematic of a separation scheme for recovering ethylene and propylene. A vapor stream (2) comprised of ethylene and propylene is compressed (4) to produce a propylene rich liquid stream (6) and an ethylene rich vapor stream (7). The ethylene vapor stream (7) is treated and concentrated in a primary absorber (8) and a sponge absorber (10) to form an ethylene rich lean sponge gas (12). The lean sponge gas (12) includes other light hydrocarbons, primarily hydrogen, methane, acetylene, ethane and other contaminants such as CO, $CO_2$, and $H_2S$ that must be removed in order to produce a high purity ethylene product.

The ethylene and propylene stream may be obtained from any industrial process for producing ethylene including catalytic and thermal cracking of hydrocarbon feedstock product streams. For example, US20080078692 discloses a hydrocarbon cracking process and subsequent treatment of the effluent streams. US 20080078692 discusses various conventional terms and process steps used in processes for recovering ethylene and propylene after a hydrocarbon cracking process, see especially paragraphs 0012-0018, 0034-0041, 0045-0055, and is hereby incorporated by reference in its entirety.

The ethylene purification scheme shown in FIG. 1 includes an amine treatment unit (14) to remove $H_2S$ and $CO_2$ from the ethylene rich lean sponge gas (12) forming stream (22). Treatment in the amine treatment unit reduces the $H_2S$ to less than about 0.1 ppm and $CO_2$ to less than about 50 ppm. The stream (22) is then fed to an acetylene selective hydrogenation unit (16) to hydrogenate the acetylene into ethylene.

In the scheme shown in FIG. 1, acetylene is hydrogenated upstream of the demethanizer (18) and ethane-ethylene splitter fractionators (20). For this example, stream (22) includes sufficient hydrogen for hydrogenating the acetylene in the gas to ethylene. Hence, no additional hydrogen is required to be added to the feed stream into the acetylene selective hydrogenation unit (16). Additionally, the acetylene selective hydrogenation unit (16) normally operates above ambient temperature while the demethanizer (18) and ethane-ethylene splitter (20) typically operate sub-ambient. Positioning the CO oxidation reactor and acetylene conversion reactor upstream of the demethanizer lessens feed heating and effluent cooling duty compared to an arrangement that includes CO oxidation and acetylene conversion in the sub-ambient section of the process.

The concentration of CO in stream (22) is variable, generally in a range of 0 to 6 vol %. It is desirable to maintain the CO concentration of the stream (22) (the acetylene selective hydrogenation reactor feed stream) within a certain operating range, typically about 1 to 0.2 vol %. In general, as the CO concentration of the acetylene selective hydrogenation reactor feed stream increases, the operating window of the acetylene selective hydrogenation reactor system and the time between catalyst regenerations decreases.

The operating window is the set of operating conditions that enables selective and stable performance. Specifically, allowing complete hydrogenation of acetylene while minimizing hydrogenation of ethylene to ethane. The operating window is affected by process conditions including reactor inlet temperature, feed acetylene, hydrogen, and CO concentrations, space velocity, and catalyst type.

Thus, as discussed above, the feed stream (22) entering the acetylene selective hydrogenation unit (16) often contains unacceptably high carbon monoxide (CO) concentrations. The present invention is directed to a process of controlling or reducing the amount of CO in feed stream (22) entering an acetylene selective hydrogenation unit (16).

The feed stream (12) from the sponge absorber contains unacceptably high levels of CO. An oxidation reactor will oxidize CO in the feed stream using elemental oxygen as an oxidant: "$CO+0.5\ O_2 \rightarrow CO_2$". The CO to $CO_2$ conversion selectivity depends on the catalyst choice and composition of the feed stream. However, the feed stream (12) from the sponge absorber contains $H_2S$ which is a catalyst poison for oxidation and must be removed from the feed stream prior to entering the oxidation reactor.

Figure 2:
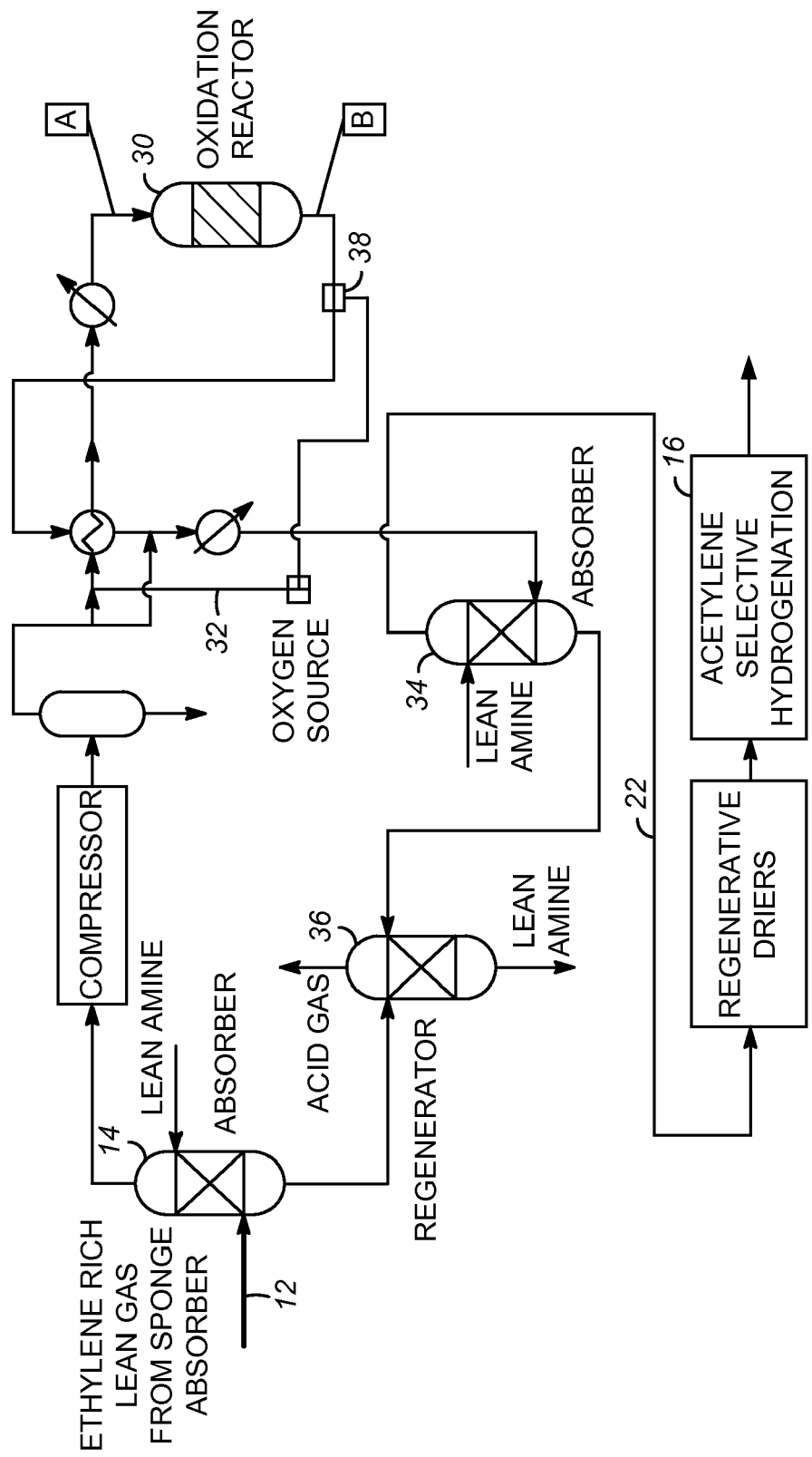
FIG. 2 is a schematic of an ethylene rich lean gas preferential CO oxidation reactor system in accordance with one embodiment of the invention.

It was discovered that placing a CO oxidation reactor downstream of the amine treatment unit (14) enables control of the CO concentration in the feed to the acetylene selective hydrogenation unit (16). As shown in FIG. 2, the ethylene rich stream (12) from the sponge absorber (not shown) flows to a first amine treatment unit (14). For this illustration, it is assumed that the first amine treatment unit (14) removes both $H_2S$ and $CO_2$ even though $CO_2$ removal upstream of the oxidation reactor is not required. Thus, the process does not require $CO_2$ removal at this stage.

The ethylene rich stream from the amine treatment unit (14), essentially $H_2S$ and $CO_2$ free, is combined with a stream (32) that provides a source of elemental oxygen, for example, air or oxygen enriched air. The combined gases A ($H_2S$ and $CO_2$-depleted stream) flow to the CO oxidation reactor (30). After CO conversion to $CO_2$, the effluent stream B (CO-depleted stream) continues to a second amine treatment unit (34) downstream of CO oxidation reactor (30). This second amine treatment unit (34) removes $CO_2$ from effluent stream B. The $CO_2$-depleted effluent then continues to the acetylene selective hydrogenation unit (16).

As also shown in FIG. 2, the amine treating arrangement uses a common amine regenerator (36) to regenerate rich amine from both the first and second amine treatment units (14) and (34). In doing so, amine treating equipment is minimized. The combination of the preferential CO oxidation reactor (30) and amine treatment unit (14) to remove $H_2S$ enables control of the CO concentration within a suitable range for subsequent acetylene conversion via conventional selective hydrogenation technology.

A sensor (38) may be placed in the effluent B stream after the CO oxidation reactor (30) to detect the amount of CO in the stream. The sensor may be placed at any position subsequent to the CO oxidation reactor where CO is present in detectable levels. The sensor may signal whether the amount of oxygen or air supplied by line (32) should be modified. The effluent stream B ideally comprises less than about 50 ppm-vol CO.

The oxidation temperature in the CO oxidation reactor (30) is typically between about 70° C. and about 160° C.

Suitable catalysts for selectively oxidizing CO using air or oxygen enriched air include, but are not limited to ruthenium metal disposed on an alumina carrier, such as those described in U.S. Pat. No. 6,299,995, hereby incorporated by reference in its entirety. The ruthenium metal comprises well dispersed ruthenium crystals having an average crystal size less than or equal to about 40 angstroms. Other suitable catalysts utilize platinum and copper.

Figure 3:
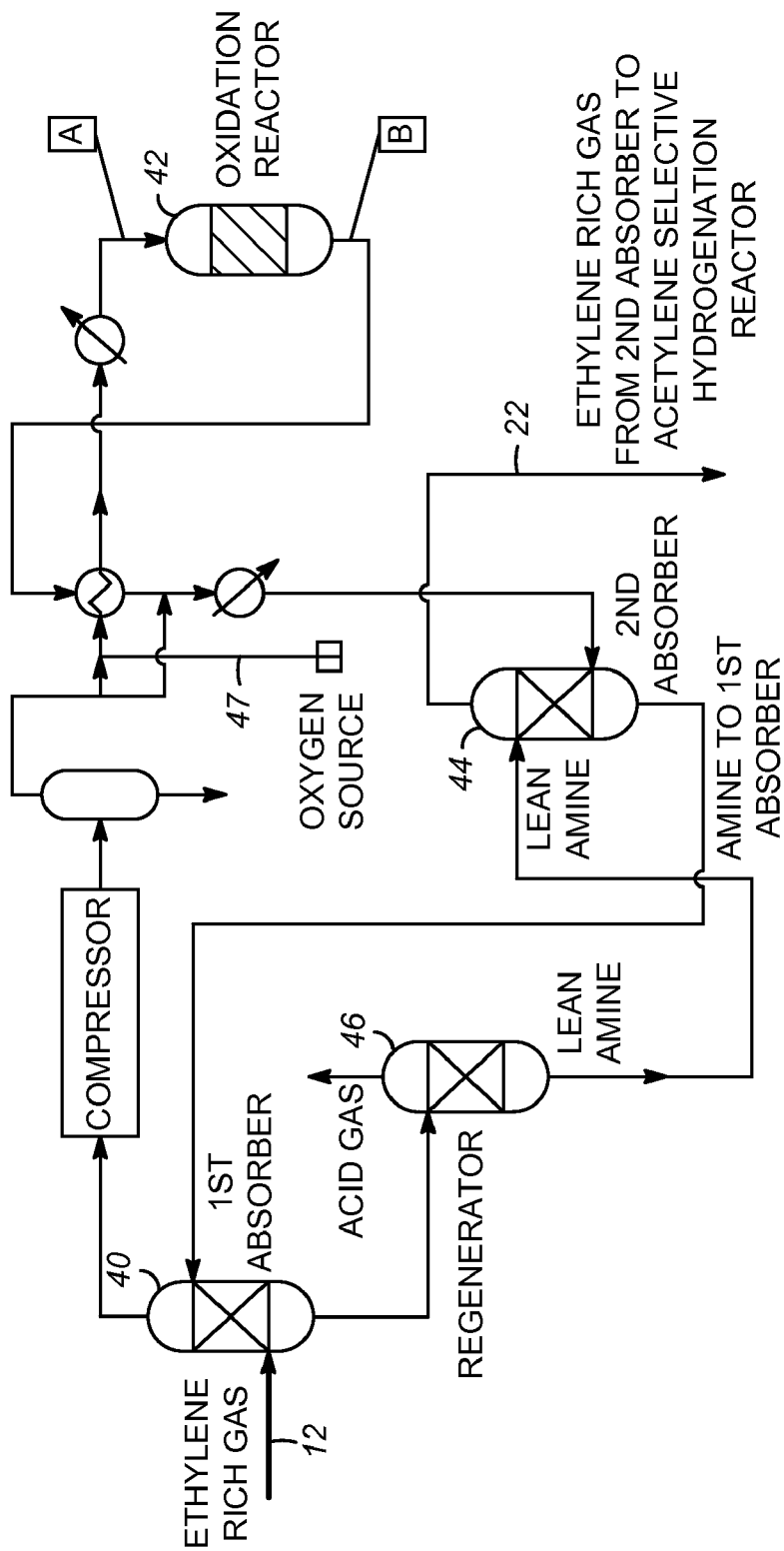
FIG. 3 is a schematic of ethylene rich lean gas preferential CO oxidation reactor system in accordance with another embodiment of the invention.

Other treatments may be used instead of amine treatment units. Alternative treatment units include absorbers with amine or solvent flow arranged in a cascading relationship. As shown in FIG. 3, an ethylene rich feed gas (12) flows into a first absorber (40) wherein $H_2S$ and $CO_2$ are removed by absorption. The ethylene rich stream from the first absorber (40), essentially $H_2S$ and $CO_2$ free, is combined with a stream (47) that provides a source of elemental oxygen. The combined gases A ($H_2S$ and $CO_2$-depleted stream) flow to the CO oxidation reactor (42). After CO conversion to $CO_2$, the effluent stream B (CO-depleted stream) continues to a second absorber (44) downstream of CO oxidation reactor (42). This second absorber (44) removes $CO_2$ from effluent stream B. The $CO_2$-depleted effluent then continues to an acetylene selective hydrogenation unit (not shown). The $CO_2$ rich amine from the second absorber (44) flows to first absorber (40). The $CO_2$ and $H_2S$ rich amine from the first absorber (40) flows to an amine regenerator (46). The lean amine from the amine regenerator (46) then flows into the second absorber (44). A CO sensor (not shown) may be placed downstream of CO oxidation reactor (42) similar to the system shown in FIG. 2 in order to control the amount of air or oxygen added to combined gases A.

In the amine treatment unit (14) shown in FIG. 1, (14) and (34) shown in FIG. 2, (40) and (44) shown in FIG. 3 selective removal of $H_2S$ and $CO_2$ can be achieved using amine-containing chemical solvents. For example, UOP AMINE GUARD™ FS may be used to remove the $H_2S$ and $CO_2$. Such solvents provide selective removal of $H_2S$ via amine selection. Other treatment units may use other chemical solvents. Chemical solvents are used to remove the acid gases by a reversible chemical reaction of the acid gases with an aqueous solution of various alkanolamines or alkaline salts in water.

Other treatment units may utilize physical solvents. With a physical solvent, the acid gas loading in the solvent is proportional to the acid gas partial pressure. For example, the UOP SELEXOL™ process may be used which uses a physical solvent made of dimethyl ether of polyethylene glycol. Chemical solvents are generally more suitable than physical or hybrid solvents for applications at lower operating pressures.

As discussed above, in accordance with the present invention, a CO oxidation reactor is placed upstream of the acetylene selective hydrogenation unit to enable control of the CO concentration within a suitable range for the acetylene selective hydrogenation reaction occurring in the acetylene selective hydrogenation unit. Further aspects of the invention are therefore directed to a method for controlling the CO concentration in an acetylene selective hydrogenation unit feed stream by preferential CO combustion (i.e. oxidation) with air or oxygen enriched air providing the oxygen.

EXAMPLES

The following examples and tables summarize the expected performance of the preferential CO oxidation reactor processing a typical ethylene-rich lean gas as shown in FIG. 2. Stream "A" is oxidation reactor feed and "B" is oxidation reactor effluent. The examples assume selectivity based on a ruthenium on alumina catalyst.

Example 1

The lean gas (i.e. $H_2S$ and $CO_2$ removed) from the amine treatment unit is mixed with air. The oxygen available for oxidizing CO is controlled to limit the CO conversion to ~50%. As shown in Table 2, the CO concentration is reduced from ~2600 ppm to ~1300 ppm.

Specifically, stream A is introduced into a CO oxidation reactor and stream B exits the reactor under the following conditions:

|  | Inlet | Outlet |
|---|---|---|
| Reactor Temperature (° F.) | 194 | 221 |
| Reactor Pressure (psia) | 246.7 |  |
| Air to Reactor (lbmol/hr) | 66 |  |

TABLE 2

| Stream "A" | | | Stream "B" | | |
|---|---|---|---|---|---|
|  | Mole Fraction | Mole % |  | Mole Fraction | Mole % |
| $H_2O$ | 0.003869 | 0.387 | H2O | 0.005189 | 0.519 |
| Oxygen | 0.001314 | 0.131 | Oxygen | 0.000000 | 0.000 |
| Nitrogen | 0.068311 | 6.831 | Nitrogen | 0.068401 | 6.840 |
| Hydrogen | 0.106621 | 10.662 | Hydrogen | 0.105446 | 10.545 |
| CO | 0.002615 | 0.262 | CO | 0.001303 | 0.130 |
| $CO_2$ | 0.000005 | 0.001 | $CO_2$ | 0.001321 | 0.132 |
| Methane | 0.248449 | 24.845 | Methane | 0.248775 | 24.878 |
| Acetylene | 0.000503 | 0.050 | Acetylene | 0.000504 | 0.050 |
| Ethylene | 0.485833 | 48.583 | Ethylene | 0.486472 | 48.647 |
| Ethane | 0.076446 | 7.645 | Ethane | 0.076546 | 7.655 |
| Propylene | 0.006035 | 0.604 | Propylene | 0.006043 | 0.604 |

Example 2

The lean gas (i.e. $H_2S$ and $CO_2$ removed) from the amine treatment unit is mixed with air. The oxygen available for oxidizing CO is controlled to limit the CO conversion to ~75%. The CO concentration is reduced from ~2600 ppm to ~600 ppm, see Table 3. Undesirable side reactions include "$H_2 + 0.5\ O_2 \rightarrow H_2O$", as well potential oxidation of light hydrocarbons including olefin products. Assuming sufficient reactant, the CO oxidation reactor essentially completely removes CO.

Stream A is introduced into a CO oxidation reactor and stream B exits the reactor under the following conditions:

|  | Inlet | Outlet |
|---|---|---|
| Reactor Temperature (° F.) | 194 | 234 |
| Reactor Pressure (psia) | 246.7 |  |
| Air to PreFOX Reactor (lbmol/hr) | 99 |  |

TABLE 3

| Stream "A" | | | Stream "B" | | |
|---|---|---|---|---|---|
|  | Mole Fraction | Mole % |  | Mole Fraction | Mole % |
| $H_2O$ | 0.003857 | 0.386 | $H_2O$ | 0.005833 | 0.583 |
| Oxygen | 0.001965 | 0.196 | Oxygen | 0.000000 | 0.000 |
| Nitrogen | 0.070561 | 7.056 | Nitrogen | 0.070700 | 7.070 |
| Hydrogen | 0.106289 | 10.629 | Hydrogen | 0.104530 | 10.453 |
| CO | 0.002607 | 0.261 | CO | 0.000644 | 0.064 |
| $CO_2$ | 0.000005 | 0.001 | $CO_2$ | 0.001973 | 0.197 |
| Methane | 0.247674 | 24.767 | Methane | 0.248161 | 24.816 |
| Acetylene | 0.000501 | 0.050 | Acetylene | 0.000502 | 0.050 |
| Ethylene | 0.484318 | 48.432 | Ethylene | 0.485271 | 48.527 |
| Ethane | 0.076207 | 7.621 | Ethane | 0.076357 | 7.636 |
| Propylene | 0.006016 | 0.602 | Propylene | 0.006028 | 0.603 |

In view of the present disclosure, it will be appreciated that other advantageous results may be obtained. Those having skill in the art, with the knowledge gained from the present disclosure, will recognize that various changes can be made in the above apparatuses and methods without departing from the scope of the present disclosure. Mechanisms used to explain theoretical or observed phenomena or results, shall be interpreted as illustrative only and not limiting in any way the scope of the appended claims.

What is claimed is:

1. A process for acetylene selective hydrogenation of an ethylene rich gas stream comprising:
    (a) supplying an ethylene rich gas comprising at least $H_2S$, $CO_2$, CO, and acetylene to a first treatment unit and removing $H_2S$ from the gas stream;
    (b) supplying the $H_2S$ depleted gas stream to an CO oxidation reactor and converting CO to $CO_2$ to form a CO-depleted gas stream;
    (c) supplying the CO-depleted gas stream to a second treatment unit to remove the $CO_2$ from the CO-depleted gas stream to form a $CO_2$-depleted gas; and
    (d) treating the CO-depleted or $CO_2$-depleted gas stream in an acetylene selective hydrogenation unit to convert the acetylene to ethylene.

2. The process of claim 1 further comprising supplying oxygen or air to the $H_2S$ depleted gas stream prior to the CO oxidation reactor.

3. The process of claim 2 further comprising detecting an amount of CO in the CO-depleted gas stream with a sensor positioned downstream of the CO oxidation reactor and controlling the supply of oxygen or air to the $H_2S$ depleted gas stream based on the amount of CO detected.

4. The process of claim 1 wherein the CO oxidation reactor comprises a catalyst.

5. The process of claim 4 wherein the catalyst comprises an active material selected from the group consisting of ruthenium, copper, and platinum on a substrate selected from the group consisting of alumina, titania, and silica.

6. The process of claim 5 wherein the catalyst is ruthenium on alumina.

7. The process of claim 1 further comprising utilizing a solvent in the first treatment unit, the second treatment unit, or both.

8. The process of claim 7 further comprising regenerating the solvent.

9. The process of claim 8 further comprising regenerating solvents from the first treatment unit and the second treatment unit in single regenerator.

10. The process of claim 8 further comprising regenerating a flow of $CO_2$ and $H_2S$ rich solvent stream from the first treatment unit and flowing the regenerated stream to the second treatment unit.

\* \* \* \* \*